(12) United States Patent
Axelrod et al.

(10) Patent No.: US 8,857,275 B2
(45) Date of Patent: Oct. 14, 2014

(54) NEMS SENSORS FOR CELL FORCE APPLICATION AND MEASUREMENT

(75) Inventors: Blake Waters Axelrod, Sierra Madre, CA (US); Paula Popescu, Pasadena, CA (US); Michael L. Roukes, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 54 days.

(21) Appl. No.: 13/460,969

(22) Filed: May 1, 2012

(65) Prior Publication Data

US 2013/0133439 A1 May 30, 2013

Related U.S. Application Data

(60) Provisional application No. 61/481,510, filed on May 2, 2011.

(51) Int. Cl.
*G01L 1/22* (2006.01)
*G01N 33/50* (2006.01)

(52) U.S. Cl.
CPC ............... *G01L 1/22* (2013.01); *G01N 33/502* (2013.01); *G01N 33/5073* (2013.01); *Y10S 977/724* (2013.01); *Y10S 977/958* (2013.01); *Y10S 977/956* (2013.01)
USPC ................ 73/862.627; 435/287.1; 977/724; 977/958; 977/956

(58) Field of Classification Search
USPC .......... 73/862.627; 435/287.1; 977/724, 958, 977/956
See application file for complete search history.

(56) References Cited

U.S. PATENT DOCUMENTS

| 4,711,820 | A  | 12/1987 | Arkles et al. |
| 4,935,345 | A  | 6/1990  | Guilbeau et al. |
| 6,408,878 | B2 | 6/2002  | Unger et al. |
| 6,540,895 | B1 | 4/2003  | Spence et al. |
| 6,575,020 | B1 | 6/2003  | de Charmoy Grey et al. |
| 6,793,753 | B2 | 9/2004  | Unger et al. |
| 6,899,137 | B2 | 5/2005  | Unger et al. |
| 6,929,030 | B2 | 8/2005  | Unger et al. |

(Continued)

FOREIGN PATENT DOCUMENTS

| WO | 94/28372 | 12/1994 |
| WO | 02/12443 | 2/2002 |

(Continued)

OTHER PUBLICATIONS

B. W. Chui, T. W. Kenny, H. J. Mamin, B. D. Terris, and D. Rugar, "Independent detection of vertical and lateral forces with a sidewall-implanted dual-axis piezoresistive cantilever," Applied Physics Letters, vol. 72, No. 11, Mar. 16, 1998, pp. 1388-1390.*

(Continued)

*Primary Examiner* — Lisa Caputo
*Assistant Examiner* — Punam Roy
(74) *Attorney, Agent, or Firm* — Gates & Cooper LLP

(57) ABSTRACT

An apparatus, system, device, and method provide the ability to measure forces a cell exerts on its surroundings. A platform is suspended across an opening using support legs. The platform is able to move horizontally in a plane of the opening. A piezoresistive strain sensor is integrated into the platform and measures strain induced in the support legs when the platform moves horizontally thereby measuring displacement of the platform.

14 Claims, 7 Drawing Sheets

(56) References Cited

U.S. PATENT DOCUMENTS

| | | | |
|---|---|---|---|
| 7,040,338 | B2 | 5/2006 | Unger et al. |
| 7,144,616 | B1 | 12/2006 | Unger et al. |
| 7,169,314 | B2 | 1/2007 | Unger et al. |
| 7,214,298 | B2 | 5/2007 | Spence et al. |
| 7,216,671 | B2 | 5/2007 | Unger et al. |
| 7,353,705 | B2 | 4/2008 | Mori et al. |
| 7,704,745 | B2 | 4/2010 | Baudenbacher et al. |
| 7,762,719 | B2 | 7/2010 | Fon et al. |
| 8,343,778 | B2 | 1/2013 | Yu et al. |
| 8,476,005 | B2 | 7/2013 | Axelrod et al. |
| 2002/0166962 | A1 | 11/2002 | Roukes et al. |
| 2003/0062193 | A1 | 4/2003 | Thaysen et al. |
| 2004/0211243 | A1 | 10/2004 | Porter et al. |
| 2005/0014129 | A1 | 1/2005 | Cliffel et al. |
| 2005/0103996 | A1 | 5/2005 | Olin et al. |
| 2005/0161749 | A1 | 7/2005 | Yang et al. |
| 2005/0204821 | A1 | 9/2005 | Fischer et al. |
| 2006/0075803 | A1 | 4/2006 | Boisen et al. |
| 2007/0266797 | A1 | 11/2007 | Hirabayashi et al. |
| 2007/0286254 | A1 | 12/2007 | Fon et al. |
| 2010/0000292 | A1* | 1/2010 | Karabacak et al. ......... 73/24.01 |
| 2010/0024572 | A1* | 2/2010 | Roukes et al. ........... 73/862.625 |
| 2010/0233792 | A1 | 9/2010 | Begley et al. |

FOREIGN PATENT DOCUMENTS

| | | |
|---|---|---|
| WO | 03/022731 | 3/2003 |
| WO | 03/095616 | 11/2003 |
| WO | 2005/119233 | 12/2005 |
| WO | 2006/073426 | 7/2006 |

OTHER PUBLICATIONS

C. G. Galbraith and M. P. Sheetz, "A micromachined device provides a new bend on fibroblast traction forces," Proc. Natl. Acad. Sci. USA, vol. 94, pp. 9114-9118, Aug. 1997.*

S. Yang and T. Saif, "Micromachnied force sensors for the study o fcell mechanics," Review of Scientific Instruments 76, 044301 (2005).*

S. Yang and T. Saif, "Reversible and repeatable linear local cell force response under large stretches," Experimental Cell Research 305 (2005) pp. 42-50.*

Arkles, B., "Tailoring surfaces with silanes", CHEMTECH, Dec. 1977, 7(12), pp. 766-778.

Baier, V., "Highly sensitive thermopile heat power sensor for microfluid calorimetry of biochemical processes", Sensors and Actuators A, 123-124 (2005), pp. 354-359. DOI: 10.1016/j.sna.2005.05.018.

Beningo, K. A., et al., "Nascent Focal Adhesions Are Responsible for the Generation of Strong Propulsive Forces in Migrating Fibroblasts", The Journal of Cell Biology, vol. 153, No. 4, May 14, 2001, pp. 881-887.

Butcher, D. T., et al., "A tense situation: forcing tumour progression", Nat Rev Cancer, vol. 9, 108-122, Feb. 2009. DOI: 10.1038/nrc2544.

Cleland, A. N., et al., "A nanometre-scale mechanical electrometer", Nature, vol. 392, Mar. 12, 1998, pp. 160-162.

Chu, Y. S., et al., "Force measurements in E-cadherin-mediated cell doublets reveal rapid adhesion strengthened by actin cytoskeleton remodeling through Rac and Cdc42", Journal of Cell Biology, vol. 167, No. 6, pp. 1183-1194, Dec. 20, 2004, DOI: 10.1083/jcb.200403043.

D'Souza-Schorey, C., "Disassembling adherens junctions: breaking up is hard to do", TRENDS in Cell Biology, vol. 15, No. 1, Jan. 2005. DOI: 10.1016/j.tcb.2004.11.002.

De Rooij, J., et al., "Integrin-dependent actomyosin contraction regulates epithelial cell scattering", The Journal of Cell Biology, vol. 171, No. 1, Oct. 10, 2005, pp. 153-164.

Dembo, M., et al., "Stresses at the Cell-to-Substrate Interface during Locomotion of Fibroblasts", Biophysical Journal, vol. 76, Apr. 1999, pp. 2307-2316.

Engler, A. J., et al., "Matrix Elasticity Directs Stem Cell Lineage Specification", Cell 126 pp. 677-689, Aug. 25, 2006. DOI 10.1016/j.cell.2006.06.044.

Gelest Data Sheet, Applying a Silane Coupling Agent, 1999.

Harris, A. K., et al., "Silicone Rubber Substrata: A New Wrinkle in the Study of Cell Locomotion", Science, New Series, vol. 208, No. 4440, Apr. 11, 1980, pp. 177-179.

Hufnagel, L., et al., "On the mechanism of wing size determination in fly development", PNAS, Mar. 6, 2007, vol. 104, No. 10, pp. 3835-3840. DOI: 10.1073/pnas.0607134104.

Ingber, D. E., "Cellular tensegrity: defining new rules of biological design that govern the cytoskeleton", Journal of Cell Science, 104, pp. 613-627, (1993).

Ingber, D. E., "Mechanical control of tissue morphogenesis during embryological development", Int. J. Dev. Biol., 50:255-266, (2006). DOI: 10.1387/ijdb.052044di.

Johannessen, E. A., et al., "Heat conduction nanocalorimeter for pl-scale single cell measurements", Applied Physics Letters, vol. 80, No. 11, pp. 2029-2031, Mar. 18, 2002. DOI: 10.1063/1.1457532.

Kim, D. H., et al., "Microengineered Platforms for Cell Mechanobiology", Annu. Rev. Biomed. Eng., Nov. 2009, pp. 203-233, doi: 10.1146/annurev-bioeng-061008-124915.

Klein, E. A., et al., "Cell-Cycle Control by Physiological Matrix Elasticity and In Vivo Tissue Stiffening", Current Biology, 19, pp. 1511-1518, Sep. 2009. DOI: 10.1016/j.cub.2009.07.069.

Knotter, D. M., et al., "Etching Mechanism of Silicon Nitride in HF-Based Solutions", Journal of the Electrochemical Society, 148 (3), pp. F43-F46, (2001). DOI: 10.1149/1.1348262.

Landau, L. D., et al., "Theory of Elasticity", Institute of Physical Problems, U.S.S.R. Acadamy of Sciences, 1959, pp. viii, 1-14, 64-81.

Landsberg, K. P., et al., "Increased Cell Bond Tension Governs Cell Sorting at the *Drosophila* Anteroposterior Compartment Boundary", Current Biology, 19, Dec. 1, 2009, pp. 1950-1955. DOI: 10.1016/j.cub.2009.10.021.

Levental, K. R., et al., "Matrix Crosslinking Forces Tumor Progression by Enhancing Integrin Signaling", Cell 139, pp. 891-906, Nov. 25, 2009. DOI: 10.1016/j.cell.2009.10.027.

Li, M., et al., "Ultra-sensitive NEMS-based cantilevers for sensing, scanned probe and very high-frequency applications", Nature Nanotechnology, vol. 2, Feb. 2007, pp. 114-120, Jan. 28, 2007. DOI: 10.1038/nnano.2006.208.

Ling, T.G.I., et al., "Fabrication and characterization of a molecular adhesive layer for micro- and nanofabricated electrochemical electrodes", Microelectronic Engineering, 67-68, (2003), pp. 887-892. DOI: 10.1016/S0167-9317(03) 00151-5.

Lo, C. M., et al., "Cell Movement Is Guided by the Rigidity of the Substrate", Biophysical Journal, vol. 79, pp. 144-152, Jul. 2000.

Loh, O., et al., "The Potential of MEMS for Advancing Experiments and Modeling in Cell Mechanics", Experimental Mechanics, (2009), 49, pp. 105-124, DOI: 10.1007/s11340-007-9099-8.

Mamin, H. J., et al., "Sub-attonewton force detection at millikelvin temperatures", Applied Physics Letters, vol. 79, No. 20, pp. 3358-3360, Nov. 12, 2001. DOI: 10.1063/1.1418256.

Mammoto, A., et al., "Rho signaling and mechanical control of vascular development", Curr. Opin. Hematol., 15:228-234, (2008).

Mege, R.-M., et al., "Regulation of cell-cell junctions by the cytoskeleton", Current Opinion in Cell Biology, 2006, 18:541-548. DOI: 10.1016/j.ceb.2006.08.004.

Miserey-Lenkei, S., et al., "Rab and actomyosin-dependent fission of transport vesicles at the Golgi complex", Nature Cell Biology, vol. 12, No. 7, Jul. 2010, pp. 645-654+. DOI: 10.1038/ncb2067.

Mrksich, M., et al., "Controlling cell attachment on contoured surfaces with self-assembled monolayers of alkanethiolates on gold", Proc. Natl. Acad. Sci. USA, vol. 93, pp. 10775-10778, Oct. 1996.

Naik, A., et al., "Cooling a nanomechanical resonator with quantum back-action", Nature, vol. 443, Sep. 14, 2006, pp. 193-196. DOI: 10.1038/nature05027.

Omelchenko, T., et al., "Rho-dependent formation of epithelial "leader" cells during wound healing", PNAS, Sep. 16, 2003, vol. 100, No. 19, pp. 10788-10793. DOI: 10.1073/pnas.1834401100.

Paszek, M. J., et al., "The Tension Mounts: Mechanics Meets Morphogenesis and Malignancy", Journal of Mammary Gland Biology and Neoplasia, vol. 9, No. 4, Oct. 2004, pp. 325-342. DOI: 10.1007/s10911-004-1404-x.

(56) References Cited

OTHER PUBLICATIONS

Paszek, M. J., et al., "Tensional homeostasis and the malignant phenotype", Cancer Cell: Sep. 2005, vol. 8, pp. 241-254. DOI: 10.1016/j.ccr.2005.08.010.

Pitaval, A., et al., "Cell shape and contractility regulate ciliogenesis in cell cycle-arrested cells", JCB: Report, vol. 191, No. 2, Oct. 18, 2010, pp. 303-312. DOI: 10.1083/jcb.201004003.

Riveline, D., et al., "Focal Contacts as Mechanosensors: Externally Applied Local Mechanical Force Induces Growth of Focal Contacts by an mDia1-dependent and ROCK-independent Mechanism", The Journal of Cell Biology, vol. 153, No. 6, Jun. 11, 2001, pp. 1175-1185.

Rizki, A., et al., "A Human Breast Cell Model of Preinvasive to Invasive Transition", Cancer Res., 2008, 68: (5), Mar. 1, 2008. DOI: 10.1158/0008-5472.CAN-07-2225.

Roukes, M., "Nanoelectromechanical systems face the future", Physics World, pp. 25-31, Feb. 2001. ISSN: 0953-8585.

Rugar, D. et al., "Single spin detection by magnetic resonance force microscopy", Nature, vol. 430, pp. 329-332, Jul. 15, 2004.

Sabass, B., et al., "High Resolution Traction Force Microscopy Based on Experimental and Computational Advances", Biophysical Journal, vol. 94, Jan. 2008, pp. 207-220. DOI: 10.1529/biophysj.107.113670.

Sawada, Y., et al., "Force Sensing by Mechanical Extension of the Src Family Kinase Substrate p130Cas", Cell 127, pp. 1015-1026, Dec. 1, 2006. DOI: 10.1016/j.cell.2006.09.044.

Schwab, K. C., et al., "Putting Mechanics into Quantum Mechanics", Physics Today, 58, pp. 36-42, Jul. 2005.

Sniadecki, N. J., et al., "Magnetic microposts as an approach to apply forces to living cells", Proceedings of the National Academy of Sciences of the USA, vol. 104, No. 37, pp. 14553-14558, 2007.

Snow, D., et al., "Static deflection measurements of cantilever arrays reveal polymer film expansion and contraction", Journal of Colloid and Interface Science, vol. 316, pp. 687-693, 2007. DOI: 10.1016/j.jcis.2007.08.050.

Tan, J. L., et al., "Cells lying on a bed of microneedles: An approach to isolate mechanical force", PNAS, Feb. 18, 2003, vol. 100, No. 4, pp. 1484-1489. DOI: 10.1073/pnas.0235407100.

Tan, J. L., et al., "Simple Approach to Micropattern Cells on Common Culture Substrates by Tuning Substrate Wettability", Tissue Engineering, vol. 10, No. 5/6, 2004, pp. 865-872.

Thaysen, J., et al., "Polymer-based stress sensor with integrated readout", Journal of Physics D: Applied Physics, 35, pp. 2698-2703 (2002).

Tortonese, M., et al., "Atomic resolution with an atomic force microscope using piezoresistive detection", Appl. Phys. Lett., 62 (8), Feb. 22, 1993, pp. 834-836.

Ulrich, T. A., et al., "The Mechanical Rigidity of the Extracellular Matrix Regulates the Structure, Motility, and Proliferation of Glioma Cells", Cancer Res., 69: (10), May 15, 2009, pp. 4167-4174. DOI: 10.1158/0008-5472.CAN-08-4859.

Van Ruitenbeek, J. M., et al., "Adjustable nanofabricated atomic sized contacts", Review of Scientific Instruments, 67 (1), pp. 108-111, Jan. 1996.

Weaver, V. M., et al., "The development of a functionally relevant cell culture model of progressive human breast cancer", seminars in Cancer Biology, vol. 6, pp. 175-184, 1995.

Yang, Y. T., et al., "Zeptogram-Scale Nanomechanical Mass Sensing" Nano Letters, 6, (4), pp. 583-586, (2006).

Zhang, Y, et al., "Calorimetric biosensors with integrated microfluidic channels", Biosensors and Bioelectronics, 19, pp. 1733-1743 (2004). DOI: 10.1016/j.bios.2004.01.009.

Zhang, Y., "A Micromachined Thermal Sensor for Biochemical Sensing and Polymer Characterization", Dissertation, The Pennsylvania State University, Pennsylvania, Aug. 2005. ProQuest/UMI, 2005.

Zhang, Y., et al., "Thermal characterization of liquids and polymer thin films using a microcalorimeter", Applied Physics Letters 86, 034101 (2005).

Johannessen, E. A., et al., "A Suspended Membrane Nanocalorimeter for Ultralow Volume Bioanalysis", IEEE Transactions on Nanobioscience, vol. 1, No. 1, Mar. 2002, pp. 29-36.

Shin, Y. S., et al., "PDMS-based micro PCR chip with Parylene coating", Journal of Micromechanics and Microengineering 13 (2003), pp. 768-774.

\* cited by examiner

NEMS SENSORS FOR CELL FORCE APPLICATION AND MEASUREMENT

CROSS-REFERENCE TO RELATED APPLICATIONS

This application claims the benefit under 35 U.S.C. Section 119(e) of the following commonly-assigned U.S. provisional patent application(s), which is/are incorporated by reference herein:

Provisional Application Ser. No. 61/481,510, filed on May 2, 2011, by Blake W. Axelrod, Paula Popescu, and Michael L. Roukes, entitled "NEMS SENSORS FOR CELL FORCE APPLICATION,".

This application is related to the following commonly-assigned patent application(s) and patent(s), which application(s)/patent(s) are incorporated by reference herein:

U.S. Pat. No. 7,966,898, application Ser. No. 11/830,612, filed on Jul. 30, 2007, and issued on Jun. 28, 2011, by Michael L. Roukes, Chung-Wah Fon, Wonhee Lee, Hongxing Tang, Blake Waters Axelrod, and John Liang Tan, entitled "POLYMER NEMS FOR CELL PHYSIOLOGY AND MICROFABRICATED CELL POSITIONING SYSTEM,"which application claims priority to Provisional Application Ser. No. 60/834,253, filed on Jul. 28, 2006, by Michael L. Roukes, Chung-Wah Fon, Wonhee Lee, and Hongxing Tang, entitled "Vacuum-insulating polymer-based micro-biocalorimeter integrated with microfluidics", Provisional Application Ser. No. 60/834,052, filed on Jul. 28, 2006, by Blake W. Axelrod, Michael L. Roukes, and John Tan, entitled "Plastic NEMs for cell physiology", and Provisional Application Ser. No. 60/834,288, filed on Jul. 28, 2006, by Blake W. Axelrod, Michael L. Roukes, and John Tan, entitled "Microfabricated cell positioning system";

U.S. patent application Ser. No. 13/110,684, filed on May 18, 2011, by Michael L. Roukes, Chung-Wah Fon, Wonhee Lee, Hongxing Tang, Blake Waters Axelrod, and John Liang Tan, entitled "POLYMER NEMS FOR CELL PHYSIOLOGY AND MICROFABRICATED CELL POSITIONING SYSTEM FOR MICRO-BIOCALORIMETER,", which application is a divisional application of U.S. Pat. No. 7,966,898, application Ser. No. 11/830,612, filed on Jul. 30, 2007, and issued on Jun. 28, 2011, by Michael L. Roukes, Chung-Wah Fon, Wonhee Lee, Hongxing Tang, Blake Waters Axelrod, and John Liang Tan, entitled "POLYMER NEMS FOR CELL PHYSIOLOGY AND MICROFABRICATED CELL POSITIONING SYSTEM," which application claims priority to Provisional Application Ser. No. 60/834,253, filed on Jul. 28, 2006, by Michael L. Roukes, Chung-Wah Fon, Wonhee Lee, and Hongxing Tang, entitled "Vacuum-insulating polymer-based micro-biocalorimeter integrated with microfluidics", Provisional Application Ser. No. 60/834,052, filed on Jul. 28, 2006, by Blake W. Axelrod, Michael L. Roukes, and John Tan, entitled "Plastic NEMs for cell physiology", and Provisional Application Ser. No. 60/834,288, filed on Jul. 28, 2006, by Blake W. Axelrod, Michael L. Roukes, and John Tan, entitled "Microfabricated cell positioning system"; and U.S. patent application Ser. No. 12/364,666, filed on Feb. 3, 2009, by Blake W. Axelrod, Michael L. Roukes, and Jessica L. Arlett, entitled "MICROFLUIDIC EMBEDDED POLYMER NEMS FORCE SENSORS," which application claims priority to U.S. Provisional Patent Application Ser. No. 61/063,603, filed on Feb. 5, 2008, by Blake W. Axelrod and Michael L. Roukes, entitled "Microfluidic-embedded NEMS force sensors applied to high-content pharmaceutical screening."

STATEMENT REGARDING FEDERALLY SPONSORED RESEARCH AND DEVELOPMENT

The invention was made with Government support under CMMI-0900833 awarded by the National Science Foundation. The Government has certain rights in this invention.

BACKGROUND OF THE INVENTION

1. Field of the Invention

The present invention relates generally to measuring the forces a cell exerts on its surroundings, and in particular, to a NEMS (nano-electromechanical system) sensor for cell force application and measurement.

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is incorporated by reference herein.)

The ability to measure the forces a cell exerts on its surrounding may be useful in a variety of technological fields. However, the prior art has failed to provide a capability to measure such forces with a sufficient and useful resolution. To better understand such deficiencies, a description of prior art systems that could benefit from such measurements may be useful.

Mechanical cues in the form of ECM (extra cellular matrix) compliance have been shown to affect a wide range of physiological processes including stem cell differentiation [1], vascular development [2], fibroblast motility [3], glioblastoma metastasis [4] and breast cancer tumor progression including invasion and metastasis [5-7]. However, despite excellent and creative work by a number of research groups, understanding of these processes, generally referred to as mechanotransduction, remains limited to a conceptual framework supported by important but sparse instances of specific molecular information [8].

Mechanotransduction remains vaguely understood because tools that quantitatively probe the cell-ECM force balance are lacking. Although, significant progress has been made in the last 10 years as the biological community has turned its attention to these problems [9-11], large and critical areas of experiment space remain inaccessible. Of particular need are tools that directly measure the cell-ECM force balance with sufficient resolution to observe the initial ECM compliance sensing events and sufficient dynamic range to track the evolution of those events into whole cell phenotype and genotype changes, such as metastasis. Furthermore, it is insufficient to merely be able to access larger portions of the relevant experiment space, rather scalable tools that provide robust and repeatable quantitative data are needed in order to identify the critical proteins and regulatory pathways in each specific system.

In addition, cellular contractility—the internal generation of force or tension by a cell—has emerged as a critical regulator of a wide range of processes in organism development. Successful embryogenesis depends upon proper maintenance of tension and stiffness within the embryo. Tension directs stem cell differentiation and cell proliferation. Forces appear to constrain the spatial organization of cells in the formation of tissues and organs. Cancer development and metastasis also depend on internal tension. Contractility is primarily driven by actomyosin force generation, which is well understood as a standalone force generating unit. However, inside a cell, the basic actomyosin unit forms a variety of distinct force generating structures or "modules" such as cortical branched networks, transverse arcs and ventral stress fibers each of which generate distinct forces and interactions with the other force modules. The specifics of force generation and feedback by the various modules are at best poorly understood. Instrumentation has been a major hindrance. Tools that can repeatedly both measure forces and mechanically perturb sub-cellular structures with near single molecule resolution and whole cell dynamic range are needed to develop a complete and quantitative understanding of the actin cytoskeleton.

Stated another way, force production in cells has been a topic of interest for some time[12][13], but interest has increased significantly since recent demonstrations that cell contraction was involved in and even responsible for tumor formation[6-7][14-16], embryogenesis[2], stem cell differentiation[1] and organ development[17-18]. Numerous studies have been dedicated to investigating the consequences of contractility on physiology (intra-cellular organization[19], cell polarity[20], cell migration[21], cell growth rate[22], cell division orientation[23], cell positioning[24], tissue cohesion [25], tissue stiffening[5]), usually in response to RhoA activation. However, few studies have focused on the origin and exact mechanism of force production. This lack of analysis is principally due to technological limitations. Indeed, most existing force measurement methods only access the global net force exerted by the cell. They are unable to measure local intra-cellular forces or to identify which intra-cellular structure is responsible for which part of the global force produced [9-11]. However, cell polarity, cell migration or tissue stiffening, for example, most likely do not depend on contraction of the same intra-cellular structures. Stress fibers are not the only cell structure supporting mechanical loads in cells. Various force production modules exist and their respective contractile and mechanical characteristics surely have differing impacts on cell behavior. Thus, it would be beneficial to distinguish the exact role of each force production module in order to understand the physiological consequences of their specific regulation and deregulation across the broad range of effects of intra-cellular contraction.

In view of the above, what is needed is a device that is useful for measuring the forces a cell exerts on its surroundings.

SUMMARY OF THE INVENTION

Embodiments of the invention provide a device that is useful for measuring the forces a cell exerts on its surroundings. The device consists of a platform suspended across an opening using four legs. The platform is able to move horizontally in the plane of the opening. A piezoresistive strain sensor is integrated into the platform, through at least two of the legs. The strain sensor is able to measure the strain induced in the legs when the platform moves horizontally, and thus is able to measure the displacement of the platform. If the displacement of the platform is small, the displacement will depend linearly on the force applied to move the platform. The constant of proportionality can be measured or calculated before hand and thus the device can be used to measure force as well as displacement.

BRIEF DESCRIPTION OF THE DRAWINGS

Referring now to the drawings in which like reference numbers represent corresponding parts throughout.

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Structural Overview

Figure 1:
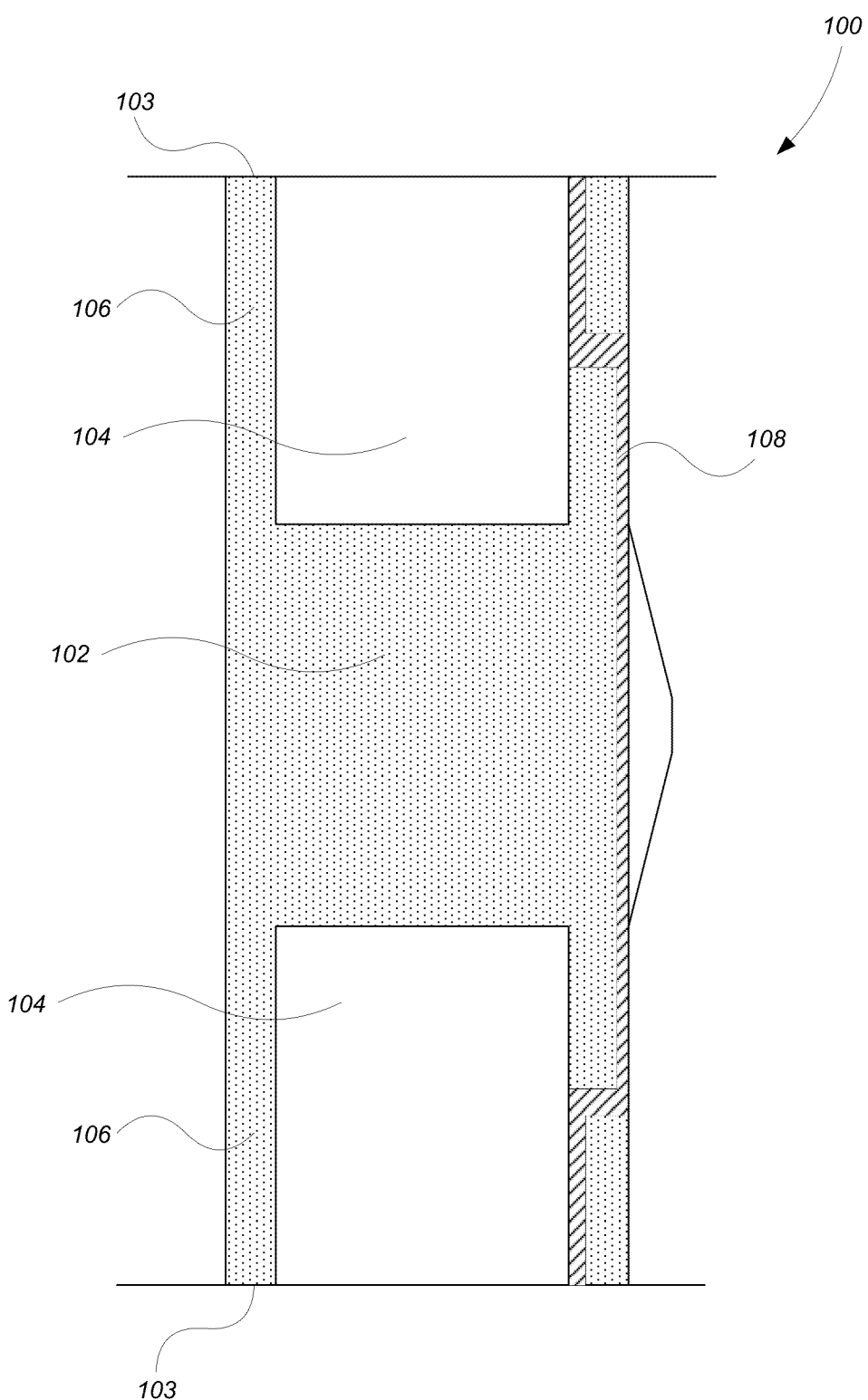
FIG. 1 illustrates a basic device for measuring the forces a cell exerts on its surroundings in accordance with one or more embodiments of the invention.

FIG. 1 illustrates a basic device for measuring the forces a cell exerts on its surroundings in accordance with one or more embodiments of the invention. The device 100 consists of a platform 102 suspended across an opening 104 (between two walls or anchor points 103) using four legs 106. The platform 102 is able to move horizontally in the plane of the opening 104. A piezoresistive strain sensor 108 (also referred to as a piezoresistive strain gauge and/or displacement sensor) is integrated into the platform 102, through at least two of the legs 106. The strain sensor 108 is able to measure the strain induced in the legs 106 when the platform 102 moves horizontally, and thus is able to measure the displacement of the platform 102. If the displacement of the platform 102 is small (e.g., roughly less than 1% of the width of the legs), the displacement will depend linearly on the force applied to move the platform 102. The constant of proportionality can be measured or calculated before measuring the displacement (or after measuring the displacement) and thus the device 100 can be used to measure force as well as displacement.

The platform 102 can be made using polymers such as SU-8, Polyimide or Parylene. The piezoresistor 108 can be fabricated from a metal such as gold, platinum, titanium, chrome and other metals. Additionally the platform 102 could be fabricated from silicon or other semiconductor material. The device 100 can be fabricated using methods described in previous the cross-referenced patents identified above (i.e., U.S. Ser. No. 12/364,666, U.S. Ser. No. 13/110,684, and U.S. Pat. No. 7,966,898) which are incorporated by reference herein.

Figure 2:
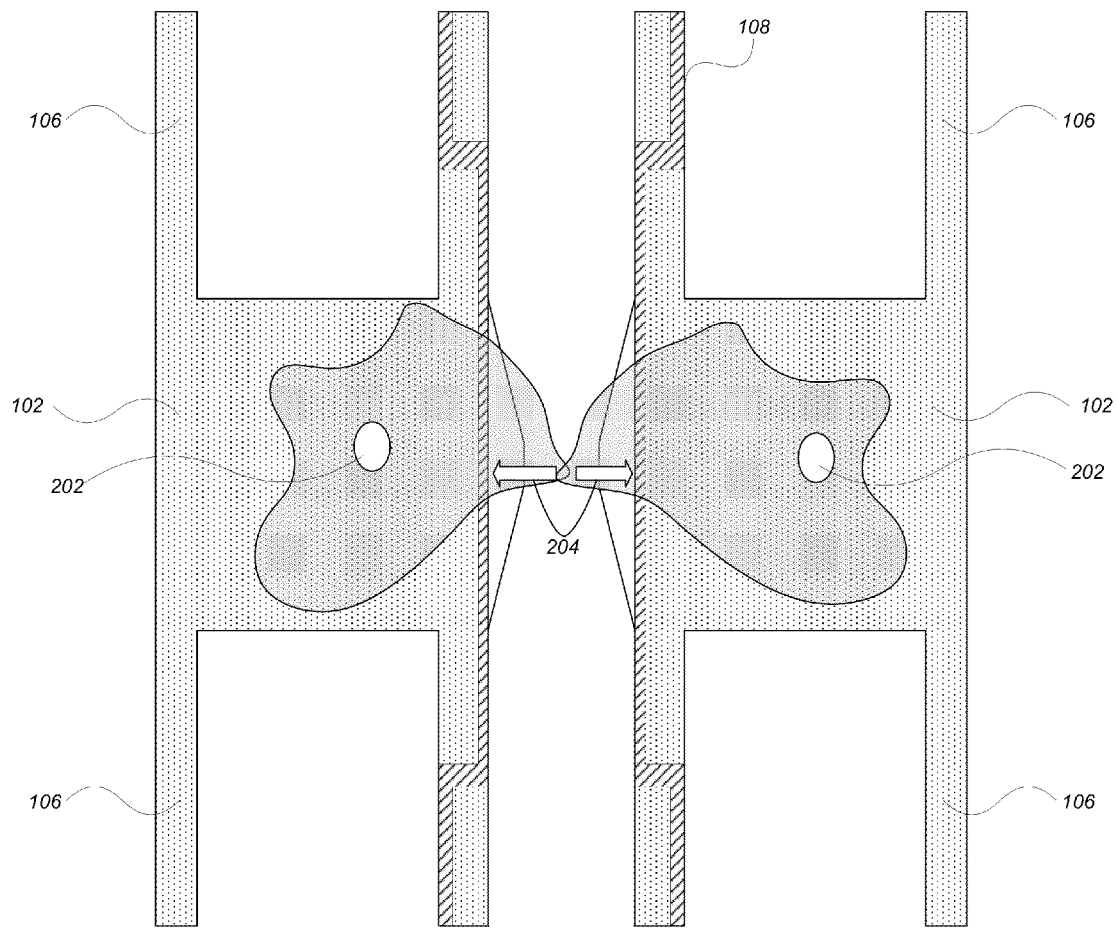
FIG. 2 illustrates an arrangement of two platforms for cell-cell force measurement in accordance with one or more embodiments of the invention.

FIG. 2 illustrates an arrangement of two platforms for cell-cell force measurement in accordance with one or more embodiments of the invention. A pair of the platforms 102 with integrated piezoresistive displacement sensors 108 can be used to measure the force that one cell 202 exerts upon another by positioning the platforms 102 close together with a cell 202 on each platform 102 and the cell-cell connection (typically referred to as an adherens junction) formed in the small gap between the platforms. The direction of cell-cell force is illustrated using arrows 204 for demonstration purposes.

In the configuration of FIG. 2, any change in force exerted between the two cells 202 will be measured as a displacement by the integrated displacement sensors 108. Alternatively, one of the platforms 102 can be fixed (prevented from moving) by not patterning legs 106. Such an arrangement may make for a simpler measurement as all of the change in force will be measured by the single movable platform 102.

Figure 3:
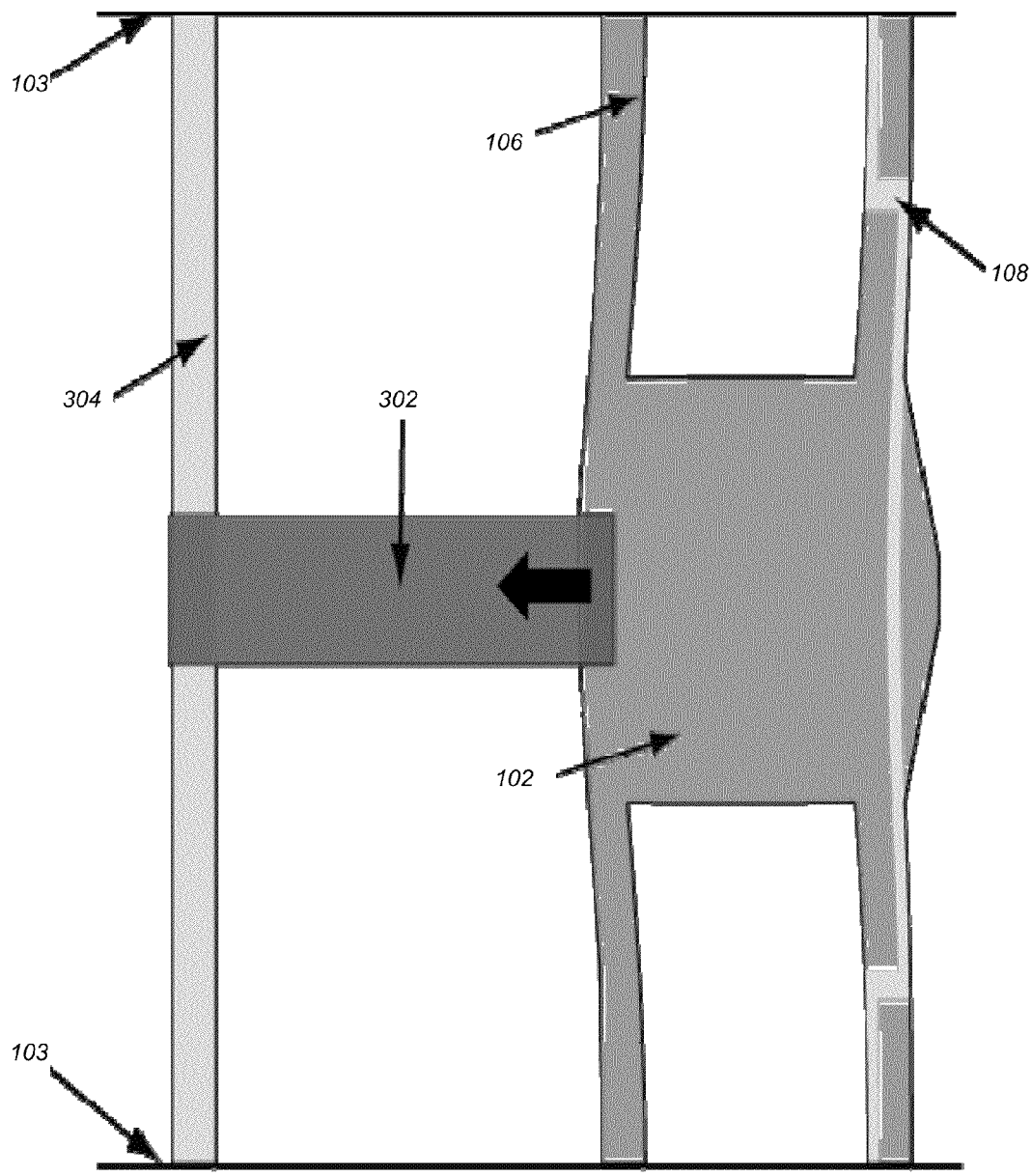
FIG. 3 illustrates a movable platform with a linear actuator attached in accordance with one or more embodiments of the invention.

It may also be useful to apply forces to a cell(s) 202 and to be able to observe the cell's 202 response. FIG. 3 illustrates a movable platform with a linear actuator attached in accordance with one or more embodiments of the invention. As illustrated, an actuator 302 can be added to the movable platform 102 with displacement sensor 108 so that the movement of the platform 102 in the horizontal plane can be controlled. The actuator 302 (e.g., a linear actuator) spans between a rigid bridge/electrode 304 and the movable platform 102. The rigid electrode 304 applies bias to the actuator 302. An electrical signal (from the rigid electrode 304) causes the actuator 302 to extend or contract and thus to move the platform 102 forward or backwards. FIG. 3 depicts the actuator 302 pulling the platform to the left. In practice, the actuator 302 can both push and pull.

The actuator 302 could be fabricated from a variety of piezoelectric materials. The actuator 302 can also be fabricated from an electroactive polymer material such as polypyrrole or polyaniline. Electroactive polymers are well suited for the purposes/applications described herein because of the large displacements that can be achieved (up to 30%), the low operating voltages (±1V) and their compatibility with ionic solutions such as cell culture media. The integrated displacement sensor 108 is important for the operation of the actuator 302 because the displacement sensor 108 allows real time measurement of the displacement of the platform 102 by the actuator 302 which can be used in a feedback loop to enable very precise displacements of the platform 102.

Figure 4:
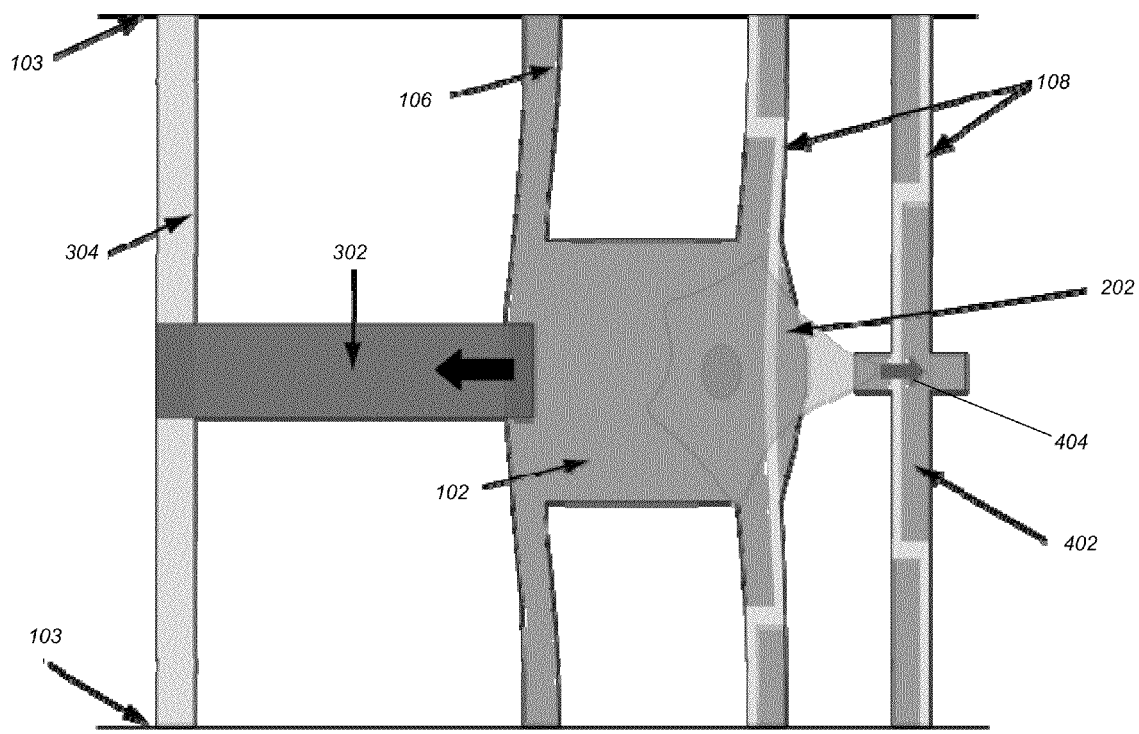
FIG. 4 illustrates a platform positioned adjacent to a force sensing beam in accordance with one or more embodiments of the invention.

The platform 102 with actuator 302 and displacement sensor 108 can be used in at least two configurations for applying force to a cell 202. In the first configuration, as illustrated in FIG. 4, the platform 102 is positioned adjacent to a force sensing beam 402 of the type described in the cross referenced patent(s)/patent application(s) above. A single cell 202 is positioned on the platform 102 and attached to the force sensing beam 402. When the platform 102 is moved, a force is applied to the cell 202 that is the product of the relative displacement of the platform 102 and beam 402 and the force constant of the beam 402. The beam 402 will then be used to measure the cell's 202 mechanical response to the applied force. Thus, FIG. 4 depicts the platform 102 being pulled to the left by the actuator 302 (e.g., a linear actuator), thus exerting a force upon the cell 202 by the beam 402 (shown with arrow 404). The displacement of the cell 202 and beam 402 are both monitored with piezoresistive sensors 108 and the cell's response to the applied force is measured.

Figure 5:
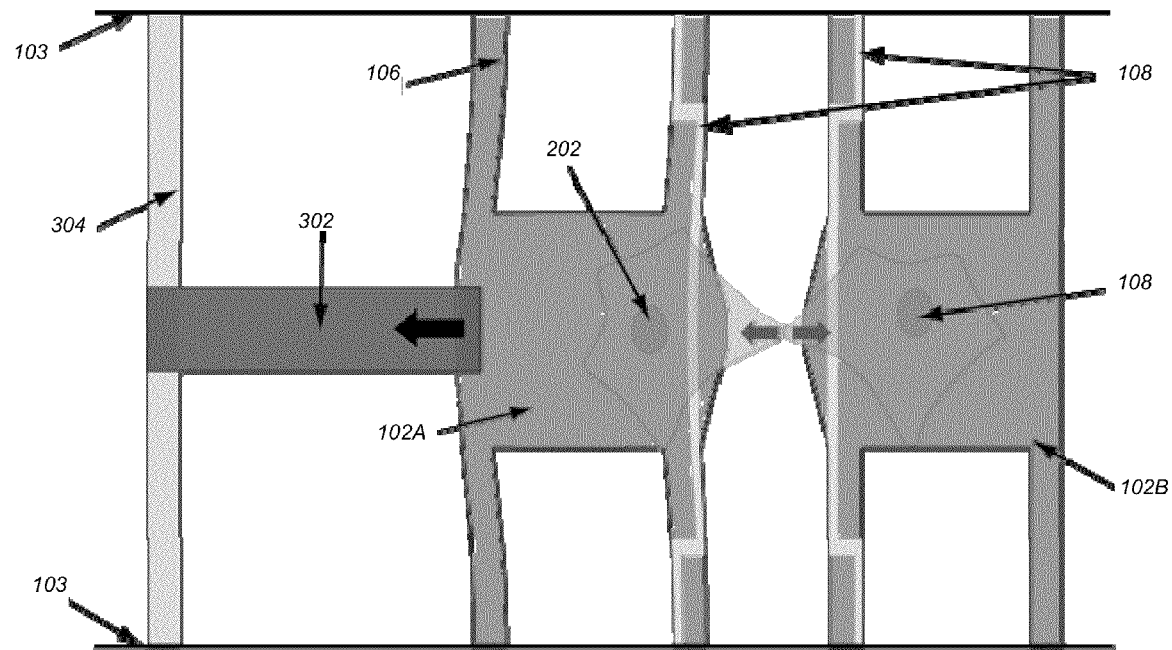
FIG. 5 illustrates two moveable platforms, one with a linear actuator, arranged in a cell-cell force measurement configuration in accordance with one or more embodiments of the invention.

The second configuration is for applying force to two cells 202 via an adherens junction as illustrated in FIG. 5. As illustrated, two moveable platforms 102A and 102B (with platform 102A coupled to a linear actuator 302) are arranged in a cell-cell force measurement configuration. The actuator 302 can push or pull the cell 202 on the left, thus exerting forces on the cell-cell connection. The displacement due to the actuator 302 is measured with one piezoresistor 108 and the force on the cell-cell junction is measured with the other piezoresistor 108. Accordingly, the configuration of FIG. 5 is similar to the cell-cell force measurement of FIG. 2 except that one platform 102A is attached to an actuator 302. The measurement works the same as the platform-beam configuration of FIG. 4 except that the force is transferred from one cell 202 to the other cell 202 through the adherens junction and the response is measured by the displacement sensor 108 in the non-actuated platform 102B.

Figure 6:
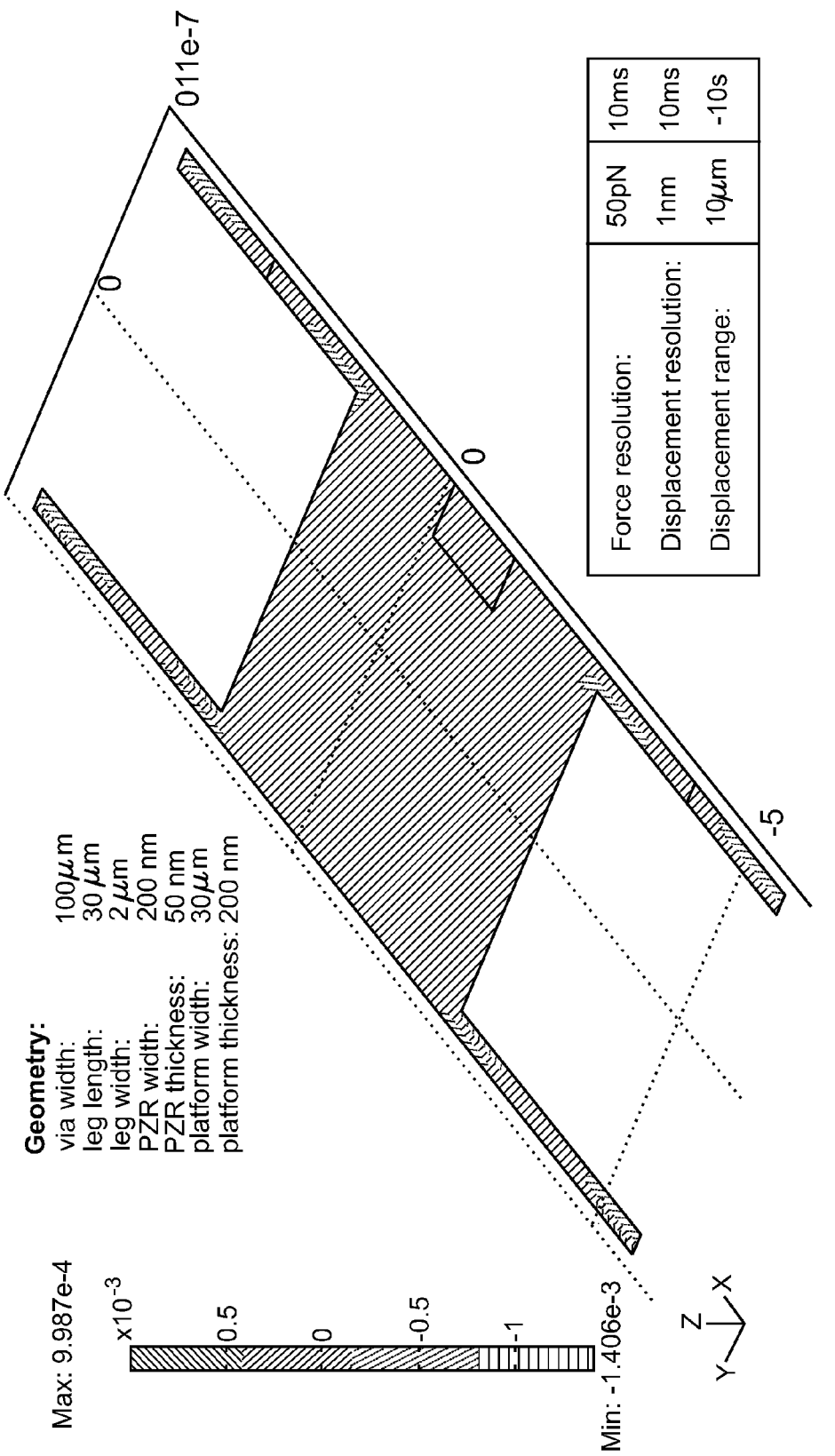
FIG. 6 illustrates the output and summary of a finite elements simulation estimating the force and displacement sensitivity of a movable platform in accordance with one or more embodiments of the invention.

FIG. 6 illustrates the output and summary of a finite elements simulation estimating the force and displacement sensitivity of a movable platform in accordance with one or more embodiments of the invention.

Logical Flow

Figure 7:
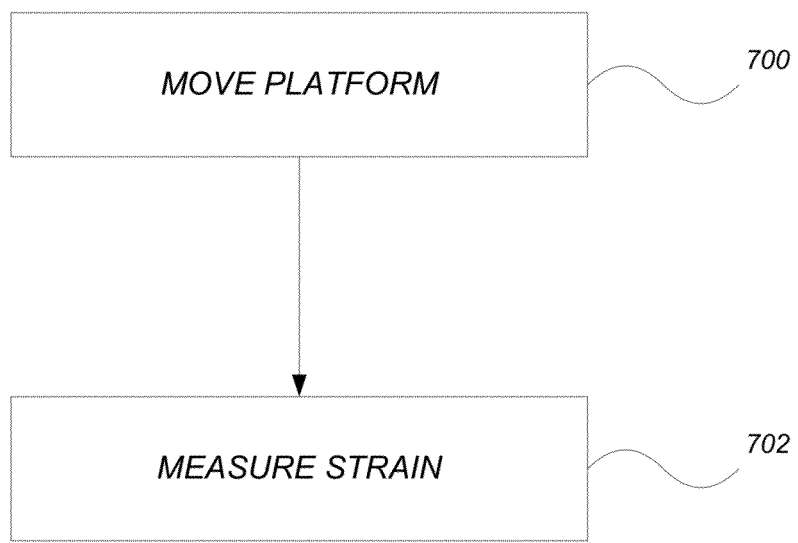
FIG. 7 illustrates the logical flow for measuring forces a cell exerts on its surroundings in accordance with one or more embodiments of the invention.

FIG. 7 illustrates the logical flow for measuring forces a cell exerts on its surroundings in accordance with one or more embodiments of the invention.

At step 700, a first platform is moved horizontally in a first plane of a first opening. The first platform is suspended across the first opening using first support legs.

At step 702, strain induced in the first support legs (when the first platform moves horizontally) is measured, thereby measuring the displacement of the first platform. The strain is measured using a first piezoresistive strain sensor that is integrated into the first platform (e.g., through at least two of the first support legs). The displacement of the first platform may depend linearly on a force applied to move the first platform. A constant of proportionality of the linear dependence may be measured and based on such a constant, the force that is applied may be measured (e.g., based on the displacement).

Step 702 may also include the movement of a second platform horizontally in the first plane of the first opening. Similar to the first platform, the second platform may be suspended across the first opening using second support legs. A cell may be placed on each platform to form an adherens junction in a gap between the two platforms. A second piezoresistive strain sensor is integrated into the second platform and used to measure strain induced in the second support legs when the second platform moves horizontally (i.e., thereby measuring displacement of the second platform). In such a device, the two platforms are positioned within a threshold distance of each other. The threshold distance will depend on the type of cell being studied. Most cell types will prefer a gap less than five (5) microns, but some larger and more motile cell types will be able to span gaps as large as ten (10) microns. A change in force exerted between the two cells (on each platform) is measured as a displacement by the two piezoresistive strain sensors. In a slightly different configuration, one of the platforms is fixed and prevented from moving.

In an addition to the use of two platforms, an actuator may be used in step 702. In such a configuration, a rigid electrode is used to apply a bias to an actuator. The actuator is configured to control the horizontal movement of the platform and spans between the rigid electrode and the platform. In one actuator based configuration, the force is transferred from one cell to another cell through an adherens junction and a response to the force is measured using the piezoresistive strain sensor in the non-actuated platform. The piezoresistive strain sensor can be utilized to perform a real-time measurement of the displacement of the platform that may be further used in a feedback loop to enable precise displacement (or control of the displacement) of the platform (e.g., by the actuator).

In a second actuator based configuration, one platform may be positioned adjacent to a force sensing beam. A single cell may be positioned on the platform and attached to the force sensing beam. When the platform is moved, a force is applied to the cell that is a product of a relative displacement of the first platform, the force sensing beam, and the force constant of the beam. The force sensing beam may be used to measure a mechanical response of the cell to the applied force.

Exemplary Applications

The ability to measure forces a cell exerts on its surroundings may be utilized in a variety of applications/scenarios/devices. Some of the potential applications/scenarios/devices are described herein. The application is not intended to be limited to the examples described herein.

Integrated Sensors and Actuators for Probing Cellular Mechanotransduction

In one or more embodiments, a single cell pico force microscopy (SCPFM) tool may utilize the invention described above. In a SCPFM, a NEMS based force sensor may be utilized to directly measure the force a cell under study exerts on its surroundings with near-single molecule force resolution and whole cell dynamic range. Embodiments of the invention may be utilized to apply precise and large mechanical perturbations to a cell under study while simultaneously measuring the cell's force response. Mechanical perturbations, by definition, are the key signaling mechanism in mechanotransduction yet existing techniques for generating mechanical perturbations remain limited [26-30]. As described above, similar to force measurement techniques, existing force application techniques either have very limited dynamic range (magnetic and optical beads), poor physiological coupling (AFM, pipette actuators [30]) or low resolution (magnetic mPADS). Embodiments of the invention integrate precision mechanical perturbation into SCPFM as well as measure cell-cell forces applied through adherens junctions. Cell-cell forces and adherens junctions play a very important role in tissue development and tumor progression [31,32].

The composite actuator/sensor device described above (e.g., see FIGS. 3-5) (also referred to as an actuated polymer plate with integrated displacement sensors [A-PPIDS]) may be configured to measure displacements as large as 10 μm (limited by the actuator size and efficiency) with ~1 nm resolution—strain stiffening during large displacements will cause non-linear force-displacement response in the plate, however the strain induced in the piezoresistor will remain linear with the displacement (though not applied force) throughout. To provide such capabilities, an electroactive polymer based linear transducer may be integrated into the fabrication process. Electroactive polymers, such as polypyrroles or polyanylines, are ideal for such an application because of their low operating voltages (~1V), large strains (up to 30%) and compatibility with ionic solutions such as growth media [33].

The A-PPIDS is used to apply force to a cell under study by first letting the cell attach to and establish a force equilibrium with an adjacent force sensing beam and then using the A-PPIDS to pull the cell away from the beam by a precisely controlled distance. The cell's mechanical response is measured throughout the process by the force sensing beam to which it is attached. The force experienced by the cell will be the product of the force sensing beam's spring constant and the difference between the displacement of the A-PPIDS and the displacement of the force sensing beam both of which will be measured in real time. A similar setup could be used to apply forces to cell-cell junctions by replacing the force sensing beam with a cell on a PPIDS.

The combination of an A-PPIDS and a force sensing beam possess an unprecedented combination of displacement application sensitivity and dynamic range as well as force measurement sensitivity and dynamic range.

Sub-Cellular Measurements and Perturbations of the Actin Cytoskeleton

One or more embodiments of the invention provide for creating reproducible actin networks within cells and/or in vitro, laser ablation and nanosurgery on sub-cellular structures such as stress fibers, integrated with a NEMS based tool capable of high resolution, high dynamic range measurement of cellular forces. The data from such an integration is then used to build detailed quantitative models of actin force generating structures. For example, precise perturbations may be used in laser nanosurgery to cut a single stress fiber. In another example, NEMS force application and pharmaceutical perturbations may be used to dissect the specific effect, crosstalk, and feedback of individual actin force modules. Based on such exemplary uses, quantitative models may be used to link actin mechanics to specific cell functions and describe how misregulation of the mechanics induces specific pathological phenotypes.

Based on the subcellular measurements, embodiments of the invention may provide a detailed, quantitative understanding of internal cellular force generation. Internal force generation is a crucial regulator of the development of embryos, stem cells, tissues, organs, and, in a negative example, cancers. Using the NEMS sensors described above, high resolution measurements may be achieved and used to develop quantitative models that link molecular mechanics to specific cell functions and describe how misregulation of the mechanics induces specific pathologies.

CONCLUSION

This concludes the description of the preferred embodiment of the invention. However, alternative embodiments may also be utilized.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

REFERENCES

[1] A. J. Engler, S. Sen, H. L. Sweeney, and D. E. Discher, "Matrix elasticity directs stem cell lineage specification" Cell 126 (4), 677 (2006). 10.1016/j.cell.2006.06.044

[2] D. E. Ingber, "Mechanical control of tissue morphogenesis during embryological development" International Journal of Developmental Biology 50 (2-3), 255 (2006). 10.1387/ijdb.052044di

[3] C. M. Lo, H. B. Wang, M. Dembo, and Y. L. Wang, "Cell movement is guided by the rigidity of the substrate" Biophysical Journal 79 (1), 144 (2000). 10.1016/S0006-3495 (00)76279-5

[4] T. A. Ulrich, E. M. D. Pardo, and S. Kumar, "The Mechanical Rigidity of the Extracellular Matrix Regulates the Structure, Motility, and Proliferation of Glioma Cells" *Cancer Research* 69 (10), 4167 (2009). 10.1158/0008-5472.can-08-4859

[5] M. J. Paszek, N. Zahir, K. R. Johnson, J. N. Lakins, G. I. Rozenberg, A. Gefen, C. A. Reinhart-King, S. S. Margulies, M. Dembo, D. Boettiger, D. A. Hammer, and V. M. Weaver, "Tensional homeostasis and the malignant phenotype" *Cancer Cell* 8 (3), 241 (2005). 10.1016/j.ccr.2005.08.010

[6] M. J. Paszek and V. M. Weaver, "The tension mounts: Mechanics meets morphogenesis and malignancy" *Journal of Mammary Gland Biology and Neoplasia* 9 (4), 325 (2004). 10.1007/s10911-004-1404-x

[7] A. Rizki, V. M. Weaver, S. Y. Lee, G. I. Rozenberg, K. Chin, C. A. Myers, J. L. Bascom, J. R. Semeiks, L. R. Grate, I. S. Man, A. D. Borowsky, R. A. Jensen, M. O. Idowu, F. Chen, D. J. Chen, O. W. Petersen, J. W. Gray, and M. J. Bissell, "A human breast cell model of preinvasive to invasive transition" *Cancer Research* 68 (5), 1378 (2008). 10.1158/0008-5472.can-07-2225

[8] Y. Sawada, M. Tamada, B. J. Dubin-Thaler, O. Cherniayskaya, R. Sakai, S. Tanaka, and M. P. Sheetz, "Force sensing by mechanical extension of the Src family kinase substrate p130Cas" *Cell* 127 (5), 1015 (2006). 10.1016/j.cell.2006.09.044

[9] M. Dembo and Y. L. Wang, "Stresses at the cell-to-substrate interface during locomotion of fibroblasts" *Biophysical Journal* 76 (4), 2307 (1999). 10.1016/S0006-3495(99)77386-8

[10] J. L. Tan, J. Tien, D. M. Pirone, D. S. Gray, K. Bhadriraju, and C. S. Chen, "Cells lying on a bed of microneedles: An approach to isolate mechanical force" *Proceedings of the National Academy of Sciences of the United States of America* 100 (4), 1484 (2003). 10.1073/pnas.0235407100

[11] B. Sabass, M. L. Gardel, C. M. Waterman, and U.S. Schwarz, "High resolution traction force microscopy based on experimental and computational advances" *Biophysical Journal* 94 (1), 207 (2008). 10.1529/biophysj.107.113670

[12] Harris, A. K., Wild, P., & Stopak, D. SILICONE-RUBBER SUBSTRATA—NEW WRINKLE IN THE STUDY OF CELL LOCOMOTION. *Science* 208 (4440), 177 (1980).

[13] Ingber, D. E. CELLULAR TENSEGRITY—DEFINING NEW RULES OF BIOLOGICAL DESIGN THAT GOVERN THE CYTOSKELETON. *Journal of Cell Science* 104, 613 (1993).

[14] Weaver, V. M. et al. THE DEVELOPMENT OF A FUNCTIONALLY RELEVANT CELL-CULTURE MODEL OF PROGRESSIVE HUMAN BREAST-CANCER. *Seminars in Cancer Biology* 6 (3), 175 (1995).

[15] Levental, K. R. et al. Matrix crosslinking forces tumor progression by enhancing integrin signaling. *Cell* 139 (5), 891 (2009).

[16] Butcher, D. T., Alliston, T., & Weaver, V. M. A tense situation: forcing tumour progression. *Nat Rev Cancer* 9 (2), 108 (2009).

[17] Hufnagel, L. et al. On the mechanism of wing size determination in fly development. *Proceedings of the National Academy of Sciences of the United States of America* 104 (10), 3835 (2007).

[18] Mammoto, A., Mammoto, T., & Ingber, D. E. Rho signaling and mechanical control of vascular development. *Current Opinion in Hematology* 15 (3), 228 (2008).

[19] Miserey-Lenkei, S. et al. Rab and actomyosin-dependent fission of transport vesicles at the Golgi complex. *Nat Cell Biol* 12 (7), 645.

[20] Pitaval, A., Tseng, Q., Bornens, M., & Thery, M. Cell shape and contractility regulate ciliogenesis in cell cycle arrested cells. *The Journal of Cell Biology* in press (2010).

[21] Beningo, K. A. et al. Nascent focal adhesions are responsible for the generation of strong propulsive forces in migrating fibroblasts. *J Cell Biol* 153 (4), 881 (2001).

[22] Klein, E. A. et al. Cell-cycle control by physiological matrix elasticity and in vivo tissue stiffening. *Curr Biol* 19 (18), 1511 (2009).

[23] Omelchenko, T. et al. Rho-dependent formation of epithelial "leader" cells during wound healing. *Proc Natl Acad Sci USA* 100 (19), 10788 (2003).

[24] Landsberg, K. P. et al. Increased cell bond tension governs cell sorting at the Drosophila anteroposterior compartment boundary. *Curr Biol* 19 (22), 1950 (2009).

[25] de Rooij, J. et al. Integrin-dependent actomyosin contraction regulates epithelial cell scattering. *J Cell Biol* 171 (1), 153 (2005).

[26] D. H. Kim, P. K. Wong, J. Park, A. Levchenko, and Y. Sun, "Microengineered Platforms for Cell Mechanobiology" *Annual Review of Biomedical Engineering* 11, 203 (2009). 10.1146/annurev-bioeng-061008-124915.

[27] O. Loh, A. Vaziri, and Hdsm Espinosa, "The Potential of MEMS for Advancing Experiments and Modeling in Cell Mechanics" *Experimental Mechanics* 49 (1), 105 (2009). 10.1007/s11340-007-9099-8

[28] D. Riveline, E. Zamir, N. Q. Balaban, U.S. Schwarz, T. Ishizaki, S. Narumiya, Z. Kam, B. Geiger, and A. D. Bershadsky, "Focal contacts as mechanosensors: Externally applied local mechanical force induces growth of focal contacts by an mDia1-dependent and ROCK-independent mechanism" *Journal of Cell Biology* 153 (6), 1175 (2001).

[29] N. J. Sniadecki, A. Anguelouch, M. T. Yang, C. M. Lamb, Z. Liu, S. B. Kirschner, Y. Liu, D. H. Reich, and C. S. Chen, "Magnetic microposts as an approach to apply forces to living cells" *Proceedings of the National Academy of Sciences of the United States of America* 104 (37), 14553 (2007). 10.1073/pnas.0611613104.

[30] Y. S. Chu, W. A. Thomas, O. Eder, F. Pincet, E. Perez, J. P. Thiery, and S. Dufour, "Force measurements in E-cadherin-mediated cell doublets reveal rapid adhesion strengthened by actin cytoskeleton remodeling through Rac and Cdc42" *Journal of Cell Biology* 167 (6), 1183 (2004). 10.1083/jcb.200403043.

[31] R. M. Mege, J. Gavard, and M. Lambert, "Regulation of cell-cell junctions by the cytoskeleton" *Current Opinion in Cell Biology* 18 (5), 541 (2006). 10.1016/j.ceb.2006.08.004.

[32] C. D'Souza-Schorey, "Disassembling adherens junctions: breaking up is hard to do" *Trends in Cell Biology* 15 (1), 19 (2005). 10.1016/j.tcg.2004.11.002.

[33] J. D. Madden, in *Electroactive Polymers for Robotic Applications*, edited by K. J. Kim and S. Tadokoro (Springer, London, 2007), pp. 121.

What is claimed is:

1. An apparatus for measuring forces a cell exerts on its surroundings comprising:
    a first platform suspended across a first opening between two walls or anchor points, using first support legs, wherein the first platform is able to move horizontally in a first plane of the first opening; and
    a first piezoresistive strain sensor integrated into the first platform through at least two of the first support legs, wherein the first piezoresistive strain sensor is configured to measure strain induced in the first support legs when the first platform moves horizontally thereby measuring displacement of the first platform a second platform suspended across the first opening using second support legs, wherein the second platform is able to move horizontally in the first plane of the first opening; and a second piezoresistive strain sensor integrated into the second platform, wherein the second piezresistive strain sensor is configured to measure strain induced in the second support legs when the second platform moves horizontally thereby measuring displacement of the second platform;

wherein:
the first platform and the second platform are positioned within a threshold distance of each other;
a cell is placed on each platform and an adherens junction is formed in a gap between the first platform and the second platform; and
a change in force exerted between the first cell and the second cell is measured as a displacement by the first piezoresistive strain sensor and the second piezoresistive strain sensor.

2. The apparatus of claim 1, wherein:
the displacement of the first platform depends linearly on a force applied to move the first platform;
a constant of proportionality of the linear dependence is measured; and
based on the constant of proportionality, the apparatus is used to measure the force.

3. The apparatus of claim 1, wherein the first platform or the second platform is fixed and prevented from moving.

4. The apparatus of claim 1, further comprising:
an actuator configured to control horizontal movement of the first platform, wherein:
the actuator spans between a rigid electrode and the first platform;
the rigid electrode applies bias to the actuator and the force is transferred from the first cell to the second cell through the adherens junction; and
a response to the force is measured by the second piezoresistive strain sensor in the second platform.

5. An apparatus for measuring forces a cell exerts on its surroundings comprising:
a first platform suspended across a first opening between two walls or anchor points, using first support legs, wherein the first platform is able to move horizontally in a first plane of the first opening;
a first piezoresistive strain sensor integrated into the first platform through at least two of the first support legs, wherein the first piezoresistive strain sensor is configured to measure strain induced in the first support legs when the first platform moves horizontally thereby measuring displacement of the first platform; and
an actuator configured to control horizontal movement of the first platform, wherein:
the actuator spans between a rigid electrode and the first platform; and
the rigid electrode applies bias to the actuator.

6. The apparatus of claim 5, wherein:
the first piezoresistive sensor enables real-time measurement of the displacement of the first platform; and
the real-time measurement of the displacement is used in a feedback loop to enable precise displacement of the first platform by the actuator.

7. The apparatus of claim 5, wherein:
the first platform is positioned adjacent to a force sensing beam;
a single cell is positioned on the first platform and attached to the force sensing beam;
when the first platform is moved, a force is applied to the cell that comprises a product of a relative displacement of the first platform and force sensing beam and a force constant of the beam; and
the force sensing beam is used to measure a mechanical response of the cell to the applied force.

8. A method for measuring forces a cell exerts on its surroundings comprising:
moving a first platform horizontally in a first plane of a first opening between two walls or anchor points, wherein the first platform is suspended across the first opening using first support legs; and
measuring strain induced in the first support legs when the first platform moves horizontally thereby measuring displacement of the first platform, wherein the strain is measured using a first piezoresistive strain sensor that is integrated into the first platform through at least two of the first support legs;

wherein:
the displacement of the first platform depends linearly on a force applied to move the first platform;
a constant of proportionality of the linear dependence is measured; and
based on the constant of proportionality, the force is measured.

9. A method for measuring forces a cell exerts on its surroundings comprising:
moving a first platform horizontally in a first plane of a first opening between two walls or anchor points, wherein the first platform is suspended across the first opening using first support legs;
measuring strain induced in the first support legs when the first platform moves horizontally thereby measuring displacement of the first platform, wherein the strain is measured using a first piezoresistive strain sensor that is integrated into the first platform through at least two of the first support legs;
moving a second platform horizontally in the first plane of the first opening, wherein a second platform is suspended across the first opening using second support legs;
placing a cell on each platform to form an adherens junction in a gap between the first platform and the second platform; and
measuring, using a second piezoresistive strain sensor that is integrated into the second platform, strain induced in the second support legs when the second platform moves horizontally thereby measuring displacement of the second platform;

wherein:
the first platform and the second platform are positioned within a threshold distance of each other;
a change in force exerted between the first cell and the second cell is measured as a displacement by the first piezoresistive strain sensor and the second piezoresistive strain sensor.

10. The method of claim 9, wherein the first platform or the second platform is fixed and prevented from moving.

11. The method of claim 9, further comprising:
applying bias, using a rigid electrode, to an actuator, wherein:
- the actuator is configured to control horizontal movement of the first platform;
- the actuator spans between the rigid electrode and the first platform;
- the force is transferred from the first cell to the second cell through the adherens junction; and
- measuring a response to the force using the second piezoresistive strain sensor in the second platform.

12. A method for measuring forces a cell exerts on its surroundings comprising:
- moving a first platform horizontally in a first plane of a first opening between two walls or anchor points, wherein the first platform is suspended across the first opening using first support legs; and
- measuring strain induced in the first support legs when the first platform moves horizontally thereby measuring displacement of the first platform, wherein the strain is measured using a first piezoresistive strain sensor that is integrated into the first platform through at least two of the first support legs;

wherein:
- an actuator controls horizontal movement of the first platform;
- the actuator spans between a rigid electrode and the first platform; and
- the rigid electrode applies bias to the actuator.

13. The method of claim 12, wherein:
- the first piezoresistive sensor enables real-time measurement of the displacement of the first platform; and
- the real-time measurement of the displacement is used in a feedback loop to enable precise displacement of the first platform by the actuator.

14. The method of claim 12, wherein:
- the first platform is positioned adjacent to a force sensing beam;
- a single cell is positioned on the first platform and attached to the force sensing beam;
- when the first platform is moved, a force is applied to the cell that comprises a product of a relative displacement of the first platform and force sensing beam and a force constant of the beam; and
- the force sensing beam is used to measure a mechanical response of the cell to the applied force.

* * * * *